United States Patent [19]

Hellman, Jr.

[11] Patent Number: 4,975,170
[45] Date of Patent: Dec. 4, 1990

[54] BACK SUPPORT FOR AN ELECTROPHORESIS GEL PLATE ASSEMBLY

[75] Inventor: Robert R. Hellman, Jr., Southbury, Conn.

[73] Assignee: Eastman Kodak Company, Rochester, N.Y.

[21] Appl. No.: 501,075

[22] Filed: Mar. 29, 1990

[51] Int. Cl.⁵ .......................................... G01N 27/26
[52] U.S. Cl. .......................... 204/299 R; 204/182.8; 204/180.1
[58] Field of Search ............. 204/180.1, 182.8, 299 R

[56] References Cited

U.S. PATENT DOCUMENTS

| | | | |
|---|---|---|---|
| 4,417,967 | 11/1983 | Ledley | 204/182.8 |
| 4,560,459 | 12/1985 | Hoefer | 204/182.8 |
| 4,572,671 | 2/1986 | Kaneko | 204/182.8 |
| 4,624,768 | 11/1986 | Yoshida et al. | 204/182.8 |
| 4,800,010 | 1/1989 | Hellman, Jr. | 204/299 R |
| 4,802,969 | 2/1989 | Hellman, Jr. | 204/182.8 |
| 4,865,715 | 9/1989 | Hellman, Jr. | 204/182.8 |

FOREIGN PATENT DOCUMENTS 60-215785 10/1985 Japan.
61-3045 2/1986 Japan.

*Primary Examiner*—John F. Niebling
*Assistant Examiner*—David G. Ryser
*Attorney, Agent, or Firm*—Dana M. Schmidt

[57] ABSTRACT

An improved gel plate assembly for electrophoresis, is described. It comprises glass-like sheet supports between which is placed the gel, at least the back support being a composite comprising a thermally conductive plate in contact with the glass-like sheet; and in contact with the conductive plate, a glass-like sheet that serves as a replacement support, when the composite is reversed, if the first sheet is scratched.

2 Claims, 1 Drawing Sheet

BACK SUPPORT FOR AN ELECTROPHORESIS GEL PLATE ASSEMBLY

FIELD OF THE INVENTION

The invention relates to the glass-like supports used in making a gel plate assembly for use in electrophoresis.

BACKGROUND OF THE INVENTION

Electrophoresis gel plate assemblies conventionally comprise a glass-like support on either side of a gel slab in which the electrophoresis takes place. To control temperature build-up in the slab, thermal metallic plates have been provided on the back side of at least one of the supports, for example as described in Japanese Kokai No. 60/215785. The support with the thermal plate is usually considered to be the back support. Although such assemblies have been found to operate satisfactorily, it is a problem with such assemblies that the back support glass or enamel can become damaged. Such damage, i.e., scratches, tend to interrupt the smooth surface to create an artifact that at best confuses the reading of the electrophoresed bands and at worst interferes with the movement of the bands through the gel. Damage can also lead to a direct electrical contact with the thermal plate, producing a burn. As a result, the back support has to be discarded if it is accidentally scratched, and replaced with a new one, including a new thermal plate.

Therefore, there has been a need prior to this invention to avoid replacing the entire back support, including the metallic plate, just because the glass-like material has become scratched.

SUMMARY OF THE INVENTION

I have provided a gel assembly which avoids the discard problem noted above.

More specifically, there is provided a gel assembly for use in electrophoresis, the assembly comprising a first support comprising a first sheet of glass-like insulation and a thermally conductive plate adhered on one of its major faces to one side of the sheet, a second support and a gel between the supports. The assembly is improved in that a second sheet of glass-like insulation is directly adhered by an adhesive to the major face of the thermally conductive plate opposite to the one major face of the first sheet, so that when the first sheet of glass becomes unsuitable for gel contact or electrophoresis because of scratches, the support is turned over to use the second sheet.

Accordingly, it is an advantageous feature of the invention that, when the glass of the back support becomes scratched, it need not be discarded, but only turned over for use of the opposite side.

Other advantageous features will become apparent upon reference to the following description when read in light of the attached drawings.

DESCRIPTION OF THE PREFERRED EMBODIMENTS

The invention is described in connection with the preferred embodiments, in which the insulative supports of the assembly are glass. In addition, it is useful whether the insulative support is glass or some other glass-like material, for example, enamel. Thus, as used herein, "glass-like insulation" refers to glass, enamel and other vitreous substances that are sufficiently similar to glass in properties as to provide the same insulative use in electrophoresis.

Figure 1:
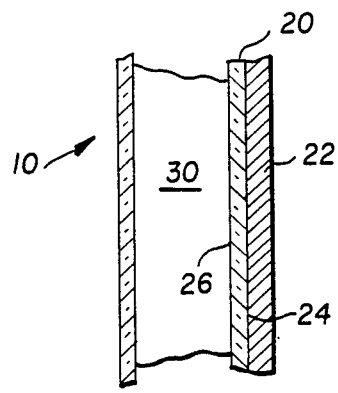
FIG. 1 is a section view of a gel plate assembly of the prior art.

FIG. 1 illustrates the problem, and is the type of construction described in the aforesaid Japanese application. That is, glass-like sheets 10 and 20 are used as the support for the electrophoresis gel 30, and a temperature-distributing thermal plate 22 is adhered to the back surface 24 of sheet 20. Such adherence can be through the use of an adhesive, or by baking sheet 20 as an enamel, onto plate 22. Plate 22 is preferably metallic. The problem arises if front surface 26 of sheet 20 becomes scratched. Since such a scratch interferes with visual observation of the results, the entire back support 20 and 22 has to be discarded.

Figure 2:
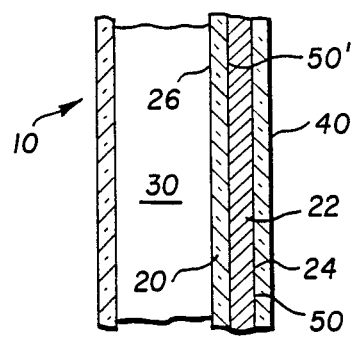
FIG. 2 is a section view of a gel plate assembly prepared in accordance with the invention.

The invention then resides in the provision, FIG. 2, on plate 22, of an additional sheet 40 of glass-like insulation of generally the same excellent light-transmissive properties as sheet 20. Preferably the attachment is via an adhesive, which can be applied at interfaces 50 and 50'. As a result, if surface 26 becomes scratched, the assembly 20-22-40 is simply reversed so that sheet 40 is placed in contact with the gel. As a result, plate 22 need not be thrown out. That is, it is cheaper and more convenient to replace sheet 20 with another sheet 40, than to replace it with another sheet 20 having a new thermal plate attached thereto.

By way of non-limiting example, sheets 20 and 40 are preferably select glass that are about 0.23 cm thick and free of scratches, chips and pits on their outside surfaces. They are bonded on their inside surfaces by polyvinyl butyrate to a core plate of anodized aluminum that has a matte, gray finish. Such a finish is considered superior to a mirrored surface as it is less likely to produce a distortion during sample loading.

The invention provides the further utility of insulating the plate 22 with the second sheet of glass 40.

The invention has been described in detail with particular reference to preferred embodiments thereof, but it will be understood that variations and modifications can be effected within the spirit and scope of the invention.

What is claimed is:

1. In a gel assembly for use in electrophoresis, said assembly comprising a first support comprising a first sheet of glass-like insulation and a thermally conductive plate adhered on one of its major faces to one side of said sheet, a second support and a gel between said supports, the improvement wherein a second sheet of glass-like insulation is directly adhered by an adhesive to the major face of said thermally conductive plate opposite to said one major face of said first sheet, so that when said first sheet of glass becomes unsuitable for gel contact because of scratches, the support is turned over to use said second sheet.

2. An assembly as defined in claim 1, wherein said plate is an aluminum sheet.

* * * * *